United States Patent [19]

de Toledo

[11] Patent Number: 5,178,158
[45] Date of Patent: Jan. 12, 1993

[54] CONVERTIBLE GUIDEWIRE-CATHETER WITH SOFT TIP

[75] Inventor: Fernando A. de Toledo, Concord, Mass.

[73] Assignee: Boston Scientific Corporation, Watertown, Mass.

[21] Appl. No.: 605,561

[22] Filed: Oct. 29, 1990

[51] Int. Cl.⁵ .............................................. A61B 5/00
[52] U.S. Cl. .................... 128/772; 128/657; 604/282; 604/280
[58] Field of Search .............. 604/282, 264, 280, 158, 604/164, 95; 128/772, 656, 657, 658

[56] References Cited

U.S. PATENT DOCUMENTS

| | | | |
|---|---|---|---|
| 3,749,086 | 7/1973 | Kline et al. | 128/772 |
| 4,003,369 | 1/1977 | Heilman et al. | 128/772 |
| 4,719,924 | 1/1988 | Crittenden et al. | 604/282 |
| 4,723,936 | 2/1988 | Buchbinder et al. | 604/95 |
| 4,739,768 | 4/1988 | Engelson | 604/282 |
| 4,763,647 | 8/1988 | Gambale | 128/657 |
| 4,779,628 | 10/1988 | Machek | 128/772 |
| 4,798,598 | 1/1989 | Bonello et al. | 128/772 |
| 4,846,186 | 7/1989 | Box et al. | 128/772 |
| 4,899,787 | 2/1990 | Ouichi et al. | 138/131 |
| 4,906,241 | 3/1990 | Noddin et al. | 606/194 |
| 4,934,380 | 6/1990 | de Toledo | 128/772 |
| 4,940,062 | 7/1990 | Hampton et al. | 128/772 |
| 4,955,862 | 9/1990 | Sepetka | 604/282 |
| 4,981,478 | 1/1991 | Evard et al. | 128/772 |

OTHER PUBLICATIONS

Sos et al., *A New Open-Ended Guidewire/Catheter*, 154 Radiology 817-818 (1985).

Primary Examiner—Max Hindenburg
Assistant Examiner—Guy V. Tucker
Attorney, Agent, or Firm—Pearson & Pearson

[57] ABSTRACT

A convertible wire for use as a guidewire or a catheter in medical applications. The convertible wire comprises a coil spring structure that extends over a proximal portion and a distal tip portion. The spring pitch at the distal tip portion is greater than the spring pitch at the proximal portion to provide greater flexibility at the distal tip portion. A polyimide sheath surround the proximal portion of the spring for increased strength. An outer polytetrafluoroethylene sheath overlies the polyimide sheath and the coil spring in the distal tip portion so the distal tip portion constitutes an atraumatic soft, floppy tip that readily travels through passages in the body.

30 Claims, 2 Drawing Sheets

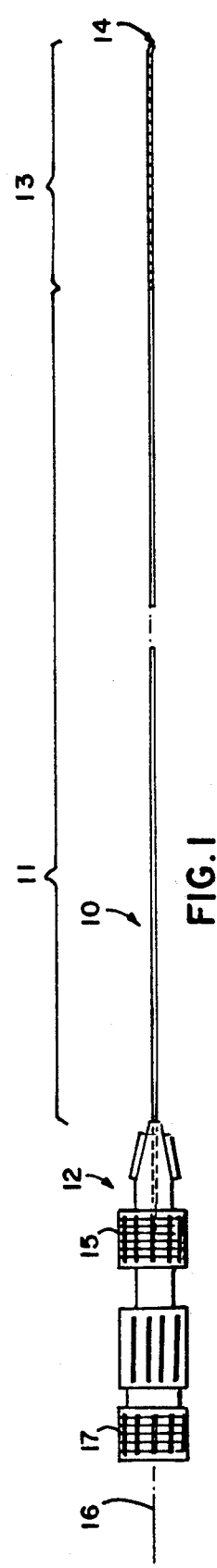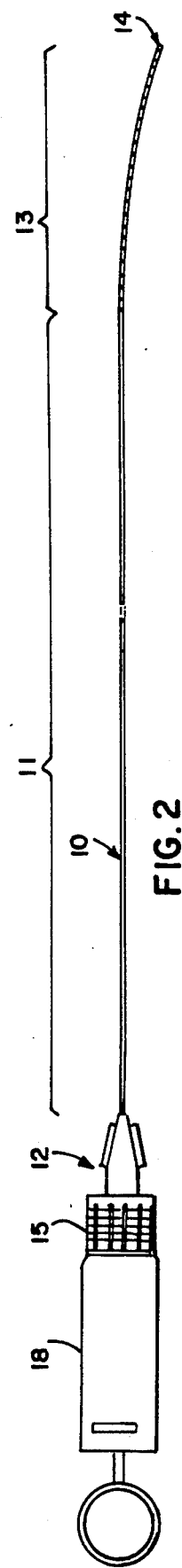

CONVERTIBLE GUIDEWIRE-CATHETER WITH SOFT TIP

BACKGROUND OF THE INVENTION

1. Field of the Invention

This invention generally relates to guidewires and catheters used in medical procedures and more specifically to a convertible wire that can operate either as a guidewire or as a catheter.

2. Description of Related Art

Medical guidewires are devices that can be navigated through narrow passages in the body. A physician controls the position and travel of a distal end of the guidewire by manipulations performed at a proximal end outside the body. Medical catheters generally comprise hollow, flexible tubes that convey fluids, such as contrast agents, embolic agents or pharmacological agents to or from a desired body vessel within the body. Guidewires and catheters sometimes have similar structures, so the term "wire" is often used to identify these devices in a generic sense. Some "wires", called "convertible wires" are adapted for use both as catheters and guidewires.

Physicians often use guidewires and catheters in combination. For example, a physician can position the tip of a guidewire at a site using its steering capability. Then the physician slides a catheter over the guidewire to the site. The physician removes the guidewire through the catheter and administers a fluid before removing the catheter.

These and other applications of guidewires and catheters in medical environments have led to several desirable, but , often antithetical, characteristics. For example, a convertible wire should have a small outer diameter to facilitate its transfer through the body with minimal trauma. However, if the outer diameter is too small, the resulting inner diameter, or lumen, limits the size of steering wires that can be accommodated in guidewire applications. In catheter applications, an unnecessarily small lumen can limit flow rates through it or the viscosity of fluids that can be accommodated by the wire. This, in turn, can limit the range of fluids administered through the catheter.

Convertible wires should be as flexible as possible so the guidewire or catheter moves easily through body passages. This can be achieved by using structures with thin walls. Yet the structure must be sufficiently strong to be safe in use, as can be achieved either by using thicker walls or internal safety wires. Such strength can dominate design criteria for catheters because fluid pressures encountered in catheters, particularly at the proximal end, can be in the order of hundreds of pounds per square inch.

The following disclose guidewires and catheters that achieve some of the foregoing desirable characteristics.

3,749,086 (1973) Kline et al
4,003,369 (1977) Heilman et al
4,719,924 (1988) Crittenden et al
4,779,128 (1988) Machek
4,798,598 (1989) Bonello et al
4,846,186 (1989) Box et al Article Sos et al, *A New Open-ended Guidewire/Catheter*,
154 Radiology 817-818 (1985)

U.S. application Ser. No. 07/276,106 filed Nov. 23, 1988 by Fernando Alvarez de Toledo for Small Diameter Guidewires of Multi-Filar Cross-Wound Coils, now U.S. Pat. No. 5,065,769 issued Nov. 19, 1991 which in turn is a continuation-in-part of Ser. No. 710514 filed Mar. 21, 1988 and issued as U.S. Pat. No. 4,932,419 on Jun. 12, 1990 titled Multifilar, Cross-Wound Coil for Medical Devices.

Kline et al d a spring guide that has closures at both ends, an elongated helically wound spring body and a composite internal core that facilitate flexing of a distal tip portion. The distal portion is made relatively more flexible than the proximal portion by a second spring that is coiled counter to that of a spring body. A plastic sheath covers the spring body.

Heilman et al disclose a guidewire that has a wound spring body formed of rectangular wire coated with Teflon ®material prior to winding to provide an ultrasmooth surface. Alternatively the finished guidewire surface is electropolished. Special materials processing and tapering of an internal safety wire in the distal tip portion enhance distal tip portion flexibility.

Crittenden et al disclose a steerable guidewire with a solid elongated main wire or core. This core extends through a central passage defined by elongated outer and inner helical springs.

Machek discloses a catheter with a wound outer casing, an internal core wire and a safety wire. The wound outer casing has the form of a coil spring produced by winding Teflon ®-coated rectangular wire. The core wire enables physicians to insert and twist the core wire relative to the casing thereby to steer the guidewire. The safety wire provides a backup should the steering wire break. The steering and safety wires, of course, require space within the guidewire and can limit the size and range of motions of any device to be inserted through the opening.

Bonello et al disclose a catheter guide with a closed-end distal tip portion formed by a coil spring. A proximal portion connects to a control mechanism and includes a coil wire. An outer plastic coating, deposited in a gaseous phase onto the spring, seals the tube and makes it smooth. The distal tip portion has no covering and adjacent coils in the spring are spaced to improve flexibility and to facilitate the exit of fluids from the catheter at the distal tip portion.

Box et al disclose a guidewire with a flexible wire core that extends through a proximal portion to a distal region where the core is characterized by tapered sub-regions internally of a flexible coiled wire spring. The wound spring has portions with adjacent coils touching; elsewhere adjacent coils are spaced to enhance flexibility.

Sos et al disclose an open-ended convertible wire that can operate as a guidewire or a catheter. The convertible wire consists of a wound spring guide with a Teflon sheath applied over a proximal portion. A distal tip is beveled and polished like that of a conventional catheter. It has been found, however, that for given outer diameter this structure limits the size of steering wires that can be used in guidewire applications. During use as a catheter for the administration of fluids, a physician must exercise care not to over pressurize the catheter.

Alvarez de Toledo discloses a small diameter wire with a multifilar coil and a polyimide sheath overlying the proximal portion. In an application as a guidewire the distal tip portion has a closed end and includes an extension of the coils and an inner coil. A core extends through the central passage formed by the springs in the inner and outer coils. In an application as a catheter, the structure comprises a spring body and a polyimide sheath extends over the length of the wire for strength.

While each of the foregoing references discloses a structure that provides one or more particularly desirable characteristic, none of them provide all the previously described desirable characteristics. For example, Kline et al and Heilman et al, Bonello and Box disclose structures that operate only as spring guides. Sos discloses a structure that can serve as a guidewire and a catheter, but it has a lumen that is smaller than desired. Further the maximum pressure limit for the wire in catheter applications is less than pressures encountered in many catheter applications. The Alvarez de Toledo reference discloses a basic structure that can be adapted to serve as a guidewire or a catheter but the specific guidewire and catheter implementations are different structurally. Moreover, neither structure shown by Sos et al or Alvarez de Toledo facilitates the insertion of the distal tip portion through body passages, although Sos et al polish a distal portion of a convertible wire. None of the references discloses a soft floppy a traumatic tip that operates in a guidewire or catheter application without detracting from the steering and fluid administration capabilities of the wire.

SUMMARY

Therefore it is an object of this invention to provide a convertible wire for use as guidewire and catheter that is steerable and has a flexible distal tip portion.

Another object of this invention is to provide a convertible wire for use as a guidewire and catheter that has a very soft flexible tip for a traumatic use.

Still another object of this invention is to provide a convertible wire for use as a catheter and guidewire that has a large lumen.

Yet another object of this invention is to provide a convertible wire for acting as a catheter that has a larger lumen for a given outer diameter thereby to improve fluid flow through the catheter.

Yet still another object of this invention is to provide a convertible wire for use as a catheter that can withstand fluid pressures in ranges normally encountered in a wide variety of medical procedures.

In accordance with this invention a convertible wire that can act as a guidewire or catheter comprises an elongated flexible open-ended tube with an internal passage therethrough that defines proximal and distal tip portions of the convertible wire. A first flexible sheath overlies the tube in the proximal portion to enhance the strength of the proximal portion. A second sheath overlies the entire convertible wire, including the first sheath and the distal tip portion, for providing a low coefficient of friction and a soft, highly flexible distal tip portion.

BRIEF DESCRIPTION OF THE DRAWINGS

The appended claims particularly point out and distinctly claim the subject matter of this invention. The various objects, advantages and novel features of this invention will be more fully apparent from a reading of the following detailed description in conjunction with the accompanying drawings in which like reference numerals refer to like parts, and in which:

FIG. 1 is a schematic view of a convertible wire constructed in accordance with this invention adapted for use as a guidewire;

FIG. 2 is a diagrammatic view of the convertible wire of FIG. 1 adapted for use as a catheter;

DESCRIPTION OF ILLUSTRATIVE EMBODIMENTS

Figure 3:
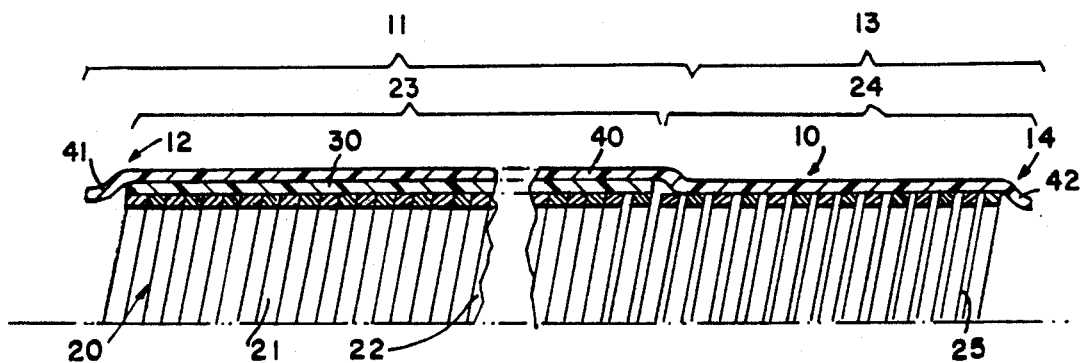
FIG. 3 is a partial cross-sectional view of portions of proximal and distal tip portions of a convertible wire constructed in accordance with this invention.

In accordance with this invention, a convertible wire 10 can be used as either a guidewire or a catheter in medical applications. For that reason the following description uses the phrase "convertible wire 10" to denote the structure generally, but independently of any application.

In FIG. 1 the convertible wire 10 serves as a guidewire and has a proximal portion 11 extending from a proximal end 12 to a distal tip portion 13 that terminates at a distal end 14. Although not shown in FIG. 1, the convertible wire 10 is open at both ends.

Still referring to FIG. 1, an adapter 15 connects to the proximal end 12 and is adapted to receive a stiffening wire 16 that is affixed to a controller 17. The stiffening wire 16 can pass through a passage in the convertible wire 10 to the proximity of the distal end 14 thus allowing the structure in FIG. 1 to act as a guidewire.

In FIG. 2 the convertible wire structure 10 is the same. It also has a proximal portion 11 extending from a proximal end 12 to a distal tip portion 13 that ends in a distal end 14. An adapter 15 is designed to receive a syringe 18 or like device for administering a fluid at the distal end 14.

FIG. 3 discloses the structure of the convertible wire 10 at both the proximal portion 11 and distal tip portion 13 in more detail. The convertible wire 10 has an inner tubular structure 20 comprising a coil of stainless steel or other wire wrapped as a spring 21 for forming an internal passage 22 through the length of the convertible wire 10. The coil 21 can comprise wire in a rectangular, circular or other cross-section although a rectangular cross-section is shown in FIG. 3. Likewise the coil can comprise a multifilar or a single wire winding. For most applications, however, a quadrifilar, rectangular stainless steel spring provides good results.

A first spring portion 23 is coextensive with a section of the proximal portion 11 and is open at the proximal end 12. The adjacent turns of the spring 21 essentially form a first spring portion 23 that has a first flexibility characteristic. A second spring section 24 that is coextensive with the distal tip portion 13, overlaps the proximal portion 11. The second spring portion 24 is an extension of the first spring portion 23 and typically is wound at the same time. However, the turns in this second spring section 24 have increased spacing or winding pitch to allow greater flexibility in the distal tip portion 13. The change in the winding pitch can be achieved by winding that portion with a different winding pitch or by elongating or stretching the turns in the second spring section 24 after it is wound. This second spring section 24 thus has second flexibility characteristics and constitutes a continuation or extension of the first spring section 23.

Still referring to FIG. 3, the convertible wire 10 shown in FIG. 3 has a plastic sheath 30, preferably a polyimide sheath, that is coextensive with and in intimate contact with the proximal portion 11. That is, the polyimide sheath 30 extends from the proximal end 12 to the distal side of the boundary between the first and second spring sections 23 and 24. The polyimide sheath has high hoop strength to constrain the individual turns in the first spring portion 23. This increases the overall pressure capability for the convertible wire 10 particularly toward the proximal end 12. Intimate contact, without the need for adhesives, can be achieved by wrapping the spring 21 on an expanded mandrel and then forcing the mandrel and coil into a tight-fitting polyimide tube. When the structure has been completed, the mandrel is withdrawn.

The convertible wire 10 in FIG. 3 also comprises sheath 40 of a polytetrafluoroethylene (e.g., Teflon ®) that extends from the proximal end 12 to the distal end 14. In some embodiments the sheath 40 forms a small overhang 41 at the proximal end 12 and a small overhang 42 at the distal end 14. The sheath 40 provides a surface with a low coefficient of friction to provide a slippery surface that facilitates the transfer of the convertible wire 10 through the patient. The sheath 40 can have a thin wall because it is not used for strength. Typically the sheath 40 is positioned over the sheath 30 and the remaining section of the coil section 24 that extends through the distal tip portion 13. Heat is applied to shrink the sheath 40 into intimate contact with the sheath 30 and the exposed portion of the second spring section 24. Such shrinking operations are well known in the art.

The combination of the thin-walled sheath 40 and the spaced turns of the second spring structure 24 provide a distal tip portion 13 that is flexible, soft and floppy. Its movement through a patient is a traumatic.

The polyimide sheath 30 over the proximal portion 11 provides sufficient bursting strength for allowing the administration of fluids in catheter application while allowing, the convertible wire 10 to be constructed with a thin spring 21. For a given outside diameter the structure shown in FIG. 1 has a larger inner diameter or lumen. This enables a larger steering wire to be utilized when the convertible wire 10 acts as a guidewire. The larger lumen permits the administration of fluids characterized with greater viscosity for a given 10 pressure of administration at the proximal end 12. Oftentimes this means that a fluid has a higher concentration of a therapeutic or other agent thereby to minimize the total volume of fluid administered to the patient for a given dose.

In one particular embodiment of this invention, a convertible wire 10 with an overall length of 145 cm has a 12 cm distal tip portion 13. The inner diameter, or lumen, is 0.027", the outer diameter, 0.038". As apparent, the total wall thickness for the coil structure 20, the polyimide sheath 30 and the outer sheath 40 is 0.0055 inches. Even with this thin-walled structure, in a catheter application, the convertible wire 10 can operate with pressures at the proximal end 12 in the order of 750 PSI or more. For a given outside diameter, an increase in lumen diameter by 35% provides a potential for up to three times the flow rate for a given pressure at the proximal end. When used as a guidewire, the larger lumen enables a heavier guidewire, including standard 0.025" guidewires, to be inserted through the central passage.

Figure 4:
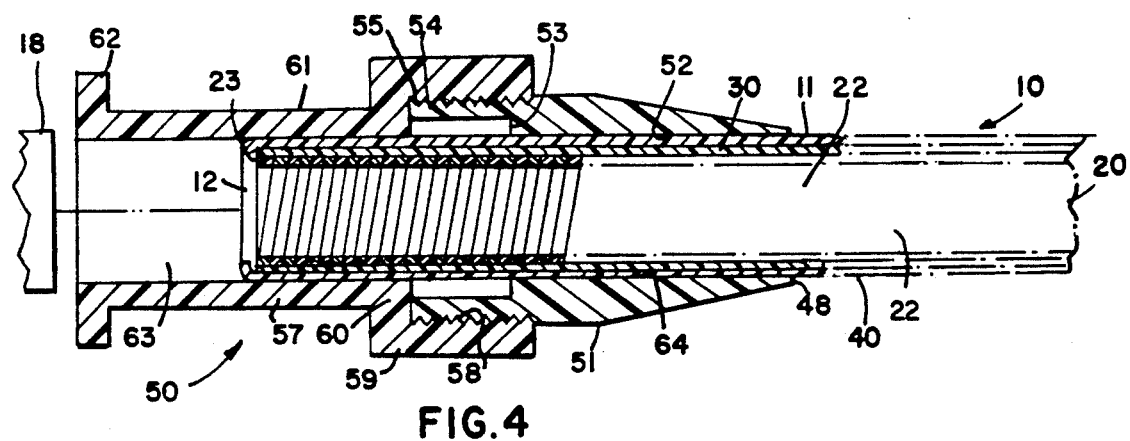
FIG. 4 is a detailed cross-sectional view of a proximal end of the structure shown in FIG. 3 to detail the construction of an adapter that is useful in accordance with the invention.

Referring to FIG. 4, a typical adapter 50 comprises a ferrule 51 that slides over the proximal end 12 of the convertible wire 10 contacting the sheath 40. Specifically, an inner surface 52 slides over the sheath 40 and forms a cavity 53 that can be filled with a compressible material (not shown). The ferrule 51 ends in a cup-shaped extension 54 with an externally threaded surface 55. A mating cup-shaped cap 57 with an internally threaded surface 58 on a ferrule connector portion 59 threads onto the extension 54. A should 60 overlies the cavity 53 and compresses any material in the cavity 53 into intimate contact with the sheath 40 thereby locking the adapter 50 on the proximal end 12.

A cylindrical body 61 extends between the shoulder 60 and a flange 62 and closely fits over the proximal end 12 of the convertible wire 10. The flange 62 and a passage 63 formed by the cylindrical body 61 communicates with the passage or lumen 22 through the convertible wire 10. When a catheter 18 is inserted in the adapter 50, fluid can pass through the passage 63 and the passage 22 to the distal end. Further details of the interface between the catheter 18 and the adapter 50 are not disclosed, because such interfaces are well known. A Leurlock hub is an example of a device with such an interface that facilitates connections of a convertible wire 10 to a wide variety of syringes, wires and other devices.

In summary, the construction shown in FIGS. 3 and 4 produces a convertible wire 10 that is readily adapted for use as a guidewire or as a catheter. The convertible wire 10 has a proximal portion 11 with an overlying polyimide sheath 30 and a thin outer Teflon sheath 40 that is additionally coextensive with a distal tip portion 13. A wound spring 21 in spring section 24 and its thin overlying Teflon sheath 40 provide a soft a traumatic floppy tip that readily passes through portions of the body. The intermediate polyimide sheath 30 over the proximal portion 11 increases the overall structural strength of the convertible wire 10 thereby to enable a reduction in wall thickness with a concomitant increase in lumen size for a given outside diameter.

This invention has been disclosed in terms of certain embodiments. It will be apparent that many modifications can be made to the disclosed apparatus without departing from the invention. For example, the preferred embodiment of the coil is a quadrifilar coil with stainless steel wire of square cross-section. Other materials, wire configurations and winding techniques can be used. Although a polyimide sheath is preferred, other plastic materials can be utilized that provide the requisite strength. Similarly the outer sheath is preferably composed of polytetrafluoroethylene, but other materials could be utilized particularly if a increased coefficient of sliding friction can be tolerated. Therefore, it is the intent of the appended claims to cover all such variations and modifications as come within the true spirit and scope of this invention.

What is claimed as new and desired to be secured by Letters Patent of the United States is:

1. A flexible, elongated open-ended convertible wire for use as a guidewire or catheter having a proximal portion and a contiguous distal tip portion and comprising:

A. flexible, elongated, open-ended tubular coil means coextensive with said proximal and distal tip portions for forming said wire with an internal passage therethrough, B. a thin-walled polyimide sheath about and coextensive with substantially all of said proximal portion of said coil means for mechanically reinforcing said coil means, and C. a thin-walled polytetrafluoroethylene sheath overlying said polyimide sheath and said coil means coextensively with said proximal and distal tip portions for forming a lubricious surface over the length of said coil means and for forming with said coil means a flexible structure at said distal tip portion.

2. A flexible, elongated, open-ended wire as recited in claim 1 wherein said polyimide sheath comprises a polyimide tube in intimate contact with said coil means over said proximal portion.

3. A flexible, elongated open-ended wire as recited in claim 1, wherein said polytetrafluoroethylene sheath comprises a polytetrafluoroethylene tube in intimate contact with said polyimide sheath and with said coil means at said distal tip portion thereof.

4. A flexible, elongated, open-ended wire as recited in claim 1 wherein said coil means comprises a wound metal coil that forms the internal passage.

5. A flexible, elongated, open-ended wire as recited in claim 4 wherein said wound metal coil comprises a multifilar winding.

6. A flexible, elongated, open-ended wire as recited in claim 4 wherein said wound metal coil has a first winding pitch at said proximal portion and a second, greater winding pitch at said distal portion.

7. A flexible, elongated, open-ended wire as recited in claim 6 wherein said wound metal coil comprises stainless steel wire.

8. A flexible, elongated, open-ended wire as recited in claim 7 wherein said wound metal spring comprises stainless steel wire with a rectangular cross-section.

9. A flexible, elongated, open-ended wire as recited in claim 4 adapted for use as a catheter and characterized by a proximal end and a distal end, said wire additionally comprising connection means affixed to said wire about said polytetrafluoroethylene sheath means at said proximal end for releasably connecting to fluid injection means for forcing a fluid means through the internal passage to be dispensed at said distal end.

10. A flexible, elongated, open-ended wire as recited in claim 4 adapted for use as a guidewire and characterized by a proximal end and a distal end, said wire additionally comprising stiffening wire means for insertion through said internal passage from said proximal end for controlling movement of said wire at said distal end.

11. A flexible wire for use as a guidewire and catheter comprising a proximal portion and a contiguous distal tip portion wherein:
A. said proximal portion includes:
i. first spring means having first flexibility characteristics for forming an internal tubular passage,
ii. a polyimide tubular sheath means about said first spring means and substantially coextensive with said proximal portion, and
iii. a polytetrafluoroethylene tubular sheath means about said polyimide tubular sheath means and coextensive with substantially of said proximal portion, and
B. said distal tip portion includes second spring means constituting an integral extension of said first spring means and having second flexibility characteristics for forming an extension of said internal tubular passage through said distal tip portion, said polytetrafluoroethylene tubular sheath means extending over said second spring means from said proximal portion in intimate contact therewith.

12. A flexible wire for serving as a flexible guidewire and catheter as recited in claim 11 wherein said second spring means has greater flexibility than said first spring means.

13. A flexible wire for serving as a flexible guidewire and catheter as recited in claim 12 wherein said first and second spring means comprise a continuously wound metal spring, said first and second spring means having a different winding pitches thereby to provide different flexibilities.

14. A flexible wire for serving as a flexible guidewire and catheter as recited in claim 13 wherein said wound metal spring comprises stainless steel wire.

15. A flexible wire for serving as a flexible guidewire and catheter as recited in claim 13 wherein said wound metal spring comprises rectangular wire.

16. A flexible wire for serving as a flexible guidewire and catheter as recited in claim 13 wherein said wound metal spring comprises stainless steel wire having a rectangular cross-section.

17. A flexible wire for serving as a flexible guidewire and catheter as recited in claim 13 wherein said polytetrafluoroethylene sheath means include portions at the end thereof that extend beyond the distal and proximal portions of said spring means respectively.

18. A flexible wire for serving as a flexible guidewire and catheter as recited in claim 17 wherein said first and second spring sections have a transition therebetween that is coextensive with a section of said polyimide sheath means at the distal end thereof.

19. A flexible wire for serving as a flexible guidewire and catheter as recited in claim 18 adapted for use as a catheter and characterized by having a proximal end and a distal end, said flexible wire additionally comprising adapter means affixed to said flexible wire about said polytetrafluoroethylene sheath means at said proximal end for releasably connecting to fluid injection means for forcing a fluid through said internal passage to be dispensed at said distal end.

20. A flexible wire for serving as a flexible guidewire and catheter as recited in claim 18 adapted for use as a guidewire and characterized by a proximal end and a distal end, said flexible wire additionally comprising stiffening wire means for insertion through said internal passage from said proximal end for controlling movement of said wire at said distal end.

21. An open-ended convertible wire for use as a guidewire and as a catheter, said convertible wire having a proximal end, a proximal portion extending from said proximal end and a distal tip portion between said proximal portion and a distal end and comprising:
A. first coiled wire means at said proximal portion for forming an elongated spring with a first degree of flexibility and an internal passage therethrough,
B. second coiled-wire means at least coextensive with the distal tip portion and extending from said first coiled-wire means to form an elongated spring section with a second degree of flexibility and an internal passage therethrough in communication with said first coiled wire means internal passage,
C. thin-walled polyimide sheath means for surrounding and contacting said first coil means and a portion of said second coil means, and
D. thin-walled polytetrafluoroethylene sheath means for overlying said polyimide sheath means and said second coiled-wire means in said distal tip portion.

22. An open-ended convertible wire for use as a guidewire and a catheter as recited in claim 21 wherein said first and second coiled-wire means comprise first and second sections respectively of a continuous wound metal spring, the winding pitch of said second section being greater than the winding pitch of said first section.

23. An open-ended convertible wire for use as a guidewire and a catheter as recited in claim 22 wherein said continuous wound metal spring comprises a multifilar winding.

24. An open-ended convertible wire for use as a guidewire and a catheter as recited in claim 22 wherein said spring comprises rectangular wire.

25. An open-ended convertible wire for use as a guidewire and a catheter as recited in claim 22 wherein said spring comprises stainless steel wire.

26. An open-ended convertible wire for use as a guidewire and a catheter as recited in claim 22 wherein said spring comprises rectangular stainless steel wire.

27. An open-ended convertible wire for use as a guidewire and a catheter as recited in claim 22 wherein a transition exists between first and second sections, said transition being positioned at the distal end of said proximal portion and coextensive with said polyimide sheath.

28. An open-ended convertible wire for use as a guidewire and a catheter as recited in claim 27 wherein said polytetrafluoroethylene sheath means has first and second portions that overhang the proximal and distal ends of said first and second coil-wire means.

29. A flexible wire for serving as a flexible guidewire and catheter as recited in claim 28 adapted for use as a catheter and characterized by having a proximal end and a distal end, said flexible wire additionally comprising adapter means affixed to said flexible wire about said polytetrafluoroethylene sheath at said proximal end for releasably connecting to fluid injection means for forcing a fluid through said internal passage to be dispensed at said distal end.

30. A flexible wire for serving as a flexible guidewire and catheter as recited in claim 28 adapted for use as a guidewire and characterized by a proximal end and a distal end, said flexible wire additionally comprising stiffening wire means for insertion through said internal passage from said proximal end for controlling movement of said wire at said distal end.

* * * * *